US012396809B2

(12) United States Patent
Sandelson et al.

(10) Patent No.: US 12,396,809 B2
(45) Date of Patent: Aug. 26, 2025

(54) SPLIT ROBOTIC REFERENCE FRAME FOR NAVIGATION

(71) Applicant: Mazor Robotics Ltd., Caesarea (IL)

(72) Inventors: Adi Sandelson, Givatayim (IL); Dor Kopito, Kibbutz Parod (IL); Nimrod Dori, Atlit (IL); Gal Eshed, Atlit (IL); Elad Ratzabi, Bait Herut (IL); Amir Keret, Atlit (IL); Ziv Seemann, Beit Ytzhack (IL); Yvan Paitel, Louisville, CO (US); Nicholas J. Rawluk, Boulder, CO (US); Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 891 days.

(21) Appl. No.: 17/580,298

(22) Filed: Jan. 20, 2022

(65) Prior Publication Data

US 2022/0241033 A1    Aug. 4, 2022

Related U.S. Application Data

(60) Provisional application No. 63/144,091, filed on Feb. 1, 2021.

(51) Int. Cl.
*A61B 34/30*    (2016.01)
*A61B 34/20*    (2016.01)

(52) U.S. Cl.
CPC ...... *A61B 34/30* (2016.02); *A61B 2034/2055* (2016.02); *A61B 2034/2072* (2016.02)

(58) Field of Classification Search
CPC . A61B 34/30; A61B 34/20; A61B 2034/2055; A61B 2034/2072; A61B 2034/2059; A61B 90/39; A61B 2090/3945; A61B 2090/3983
See application file for complete search history.

(56) References Cited

U.S. PATENT DOCUMENTS

2017/0119339 A1    5/2017  Johnson et al.
2019/0105116 A1*   4/2019  Johnson ............ A61B 17/7074
2020/0222122 A1    7/2020  Snyder et al.

FOREIGN PATENT DOCUMENTS

WO    WO 2021/252263    12/2021

OTHER PUBLICATIONS

International Search Report and Written Opinion for International (PCT) Patent Application No. PCT/IL2022/050127, dated Jul. 21, 2022, 16 pages.

* cited by examiner

*Primary Examiner* — Ankit D Tejani
*Assistant Examiner* — Joshua Brendon Solomon
(74) *Attorney, Agent, or Firm* — Sheridan Ross P.C.

(57) ABSTRACT

A robotic navigation system includes a robot base; a robotic arm with a proximal end secured to the robot base, a distal end movable relative to the proximal end, and one or more arm segments between the proximal end and the distal end; a base set of tracking markers secured to the robot base; and at least one additional set of tracking markers secured to the robotic arm.

20 Claims, 3 Drawing Sheets

SPLIT ROBOTIC REFERENCE FRAME FOR NAVIGATION

CROSS REFERENCE TO RELATED APPLICATIONS

This application claims the benefit of U.S. Provisional Application No. 63/144,091, filed on Feb. 1, 2021, and entitled "Split Robotic Reference Frame for Navigation", which application is incorporated herein by reference in its entirety.

FIELD

The present technology generally relates to robotic surgery, and relates more particularly to navigation during robotic surgery using a split robotic reference frame.

BACKGROUND

Surgical navigation systems are used to track the position of one or more objects during surgery. Surgical robots are useful for holding one or more tools or devices during a surgery, and may operate autonomously (e.g., without any human input during operation), semi-autonomously (e.g., with some human input during operation), or non-autonomously (e.g., only as directed by human input).

SUMMARY

Example aspects of the present disclosure include:

A robotic navigation system according to at least one embodiment of the present disclosure comprises a robot base; a robotic arm comprising: a proximal end secured to the robot base; a distal end movable relative to the proximal end; and one or more arm segments between the proximal end and the distal end; a base set of tracking markers secured to the robot base; at least one additional set of tracking markers secured to at least one arm segment of the one or more arm segments; and at least one sensor for detecting an arrangement of the base set of tracking markers and the at least one additional set of tracking markers.

Any of the aspects herein, wherein the at least one additional set of tracking markers comprises a first set of tracking markers secured to a first arm segment of the one or more arm segments and a second set of tracking markers secured to a second arm segment of the one or more arm segments.

Any of the aspects herein, wherein each of the base set of tracking markers, the first set of tracking markers, and the second set of tracking markers comprises at least two markers.

Any of the aspects herein, further comprising: a geometric pattern projected onto the robotic arm.

Any of the aspects herein, wherein the at least one additional set of tracking markers are distinguishable by wavelength.

Any of the aspects herein, wherein the base set of tracking markers is at least one of removably secured or fixedly secured to the robot base.

Any of the aspects herein, further comprising: at least one processor; and a memory storing instructions for execution by the at least one processor that, when executed, cause the at least one processor to: receive information about a detected arrangement of the base set of tracking markers and the at least one additional set of tracking markers from the at least one sensor; generate a virtual reference frame spanning the base set of tracking markers and the at least one additional set of tracking markers, based on the detected arrangement information; and determine a pose in space of the robotic arm using the virtual reference frame.

Any of the aspects herein, further comprising: at least one processor; and a memory storing instructions for execution by the at least one processor that, when executed, cause the at least one processor to: receive information about a detected arrangement of the base set of tracking markers and the at least one additional set of tracking markers and information about the pattern projected onto the robotic arm; and map, based on the detected arrangement and the pattern, the robotic arm.

Any of the aspects herein, wherein the at least one sensor is a first sensor, the system further comprising; a second sensor configured to provide pose information corresponding to the robotic arm, and wherein the memory stores additional instructions for execution by the at least one processor that, when executed, further cause the at least one processor to: receive pose information from the second sensor, and determine, based on the pose information, a predicted arrangement of the base set of tracking markers and the at least one additional set of tracking markers.

Any of the aspects herein, wherein the memory stores additional instructions for execution by the at least one processor that, when executed, further cause the at least one processor to: compare the detected arrangement to the predicted arrangement, the detected arrangement received from the first sensor.

Any of the aspects herein, wherein the memory stores additional instructions for execution by the at least one processor that, when executed, further cause the at least one processor to: verify the integrity of the pose information based on the comparison.

A method of utilizing a robotic reference frame for navigation according to at least one embodiment of the present disclosure comprises causing a robotic arm to contact an anatomical element; receiving information from a sensor about a detected arrangement of a base set of tracking markers and at least one additional set of tracking markers, the base set of tracking markers positioned on a base of a robot and the at least one additional set of tracking markers positioned on a corresponding at least one robotic arm segment of the robotic arm; generating a virtual reference frame based on the detected arrangement; and determining a position of the anatomical element based on the virtual reference frame.

Any of the aspects herein, wherein the determining the position of the anatomical element includes determining a pose of the anatomical element based on the virtual reference frame.

Any of the aspects herein, wherein the at least one additional set of tracking markers comprises a first set of tracking markers secured to a first arm segment of the at least one arm segment and a second set of tracking markers secured to a second arm segment of the at least one arm segment.

Any of the aspects herein, wherein each of the base set of tracking markers and the at least one additional set of tracking markers comprises at least two markers.

Any of the aspects herein, wherein the information received is received from a first sensor, and wherein the method further comprising: receiving pose information from a second sensor; determining, based on the pose information received from the second sensor, a predicted arrangement of the base set of tracking markers and the at least one additional set of tracking markers; and comparing the detected arrangement to the predicted arrangement.

Any of the aspects herein, wherein the at least one additional set of tracking markers is distinguishable by wavelength.

Any of the aspects herein, wherein the base set of tracking markers is at least one of removably secured or fixedly secured to the robot base.

A device for surgical navigation utilizing a robotic reference frame according to at least one embodiment of the present disclosure comprises at least one processor; and a memory storing instructions for execution by the at least one processor that, when executed, cause the at least one processor to: cause a robotic arm to contact an anatomical element; receive information from a sensor about a detected arrangement of a base set of tracking markers and a first set of tracking markers and information, the base set of tracking markers disposed on a base of a robot and the first set of tracking markers disposed on an arm segment of a robotic arm; generate a virtual reference frame based on the detected arrangement; and determine a pose in space of the anatomical element based on the virtual reference frame.

Any of the aspects herein, wherein the arm segment is a first arm segment of a plurality of arm segments of the robotic arm, and a second arm segment of the plurality of arm segments comprises a second set of tracking markers.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1A:
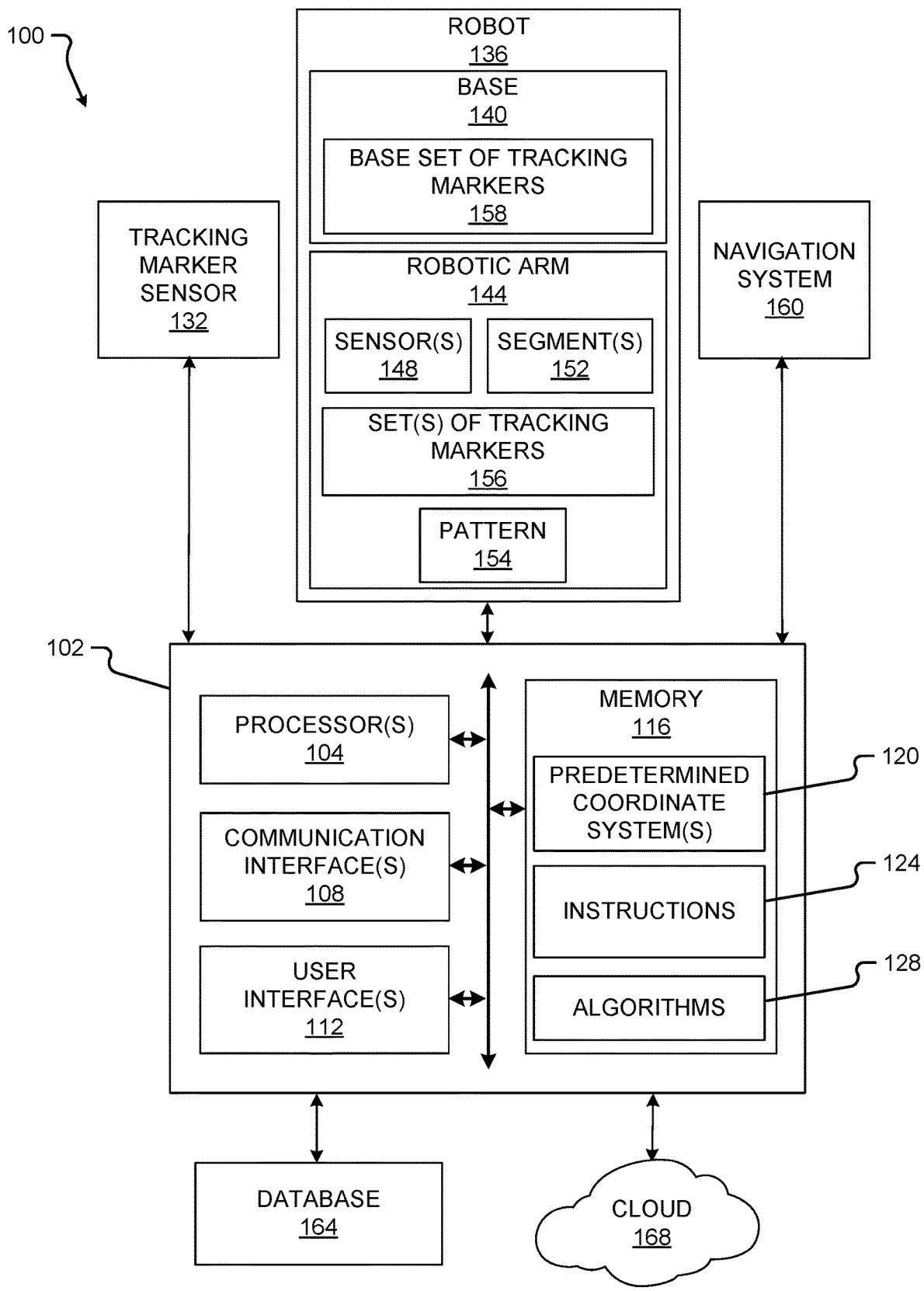
FIG. 1A is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Navigated robotic procedures may involve reference frames and trackers whose positions are detected by a tracking marker sensor. For example, a navigation system could use a camera as a tracking marker sensor, which can detect optical tracking markers on a reference frame attached to a robotic arm. With this information, the coordinate system of the robotic system can be correlated to the coordinate system of the navigation system. In other circumstances, the information from the tracking marker sensor, which can accurately determine the position and orientation of the robotic arm, can be used to calibrate the robotic system.

However, these optical systems need clear lines of sight between the cameras and the tracking markers, which can be obscured by an instrument, a tool, a surgeon, or other personnel during a surgical procedure. To overcome these problems (and others), a base set of tracking markers may be disposed at a known position on a base of the robot and at least one additional set of tracking markers may be secured to one or more robotic arm segments of a robotic arm. The base set of tracking markers and the at least one additional set of tracking markers may be combined into a "virtual reference frame". A pose in space of the robotic arm may then be determined using the virtual reference frame and information about a pose of the robotic arm. In embodiments where two or more sets of tracking markers are secured to a respective robotic arm segment, a redundancy is created and only one set of the tracking markers needs to be detected by the tracking marker sensor and combined with the base set of tracking markers. In other words, a virtual reference frame can be formed despite a partial blockage of a line of sight so long as at least one set is detectable by the tracking marker sensor.

Embodiments of the present disclosure provide for a virtual reference frame comprising a base set of tracking markers at a known, fixed position and at least one additional set of tracking markers secured to at least one robotic arm segment of one or more robotic arm segments. Embodiments of the present disclosure therefore enable a reference frame to be formed even if some tracking markers are blocked. Similarly, embodiments of the present disclosure enable verification of robotic integrity in real time by comparing robotic arm position and/or orientation information (e.g., pose information) based on sensor data to robotic arm position and/or orientation information determined using the virtual reference frame. Embodiments of the present disclosure therefore increase ease of use and decrease operation times over known navigation systems, registration procedures, and calibration operations.

Embodiments of the present disclosure provide technical solutions to the problems of (1) determining a pose of a robotic arm, anatomical element, or an object using; (2) verifying pose information received from a robotic arm; (3) obtaining line of sight of reference marker(s); and/or (4) increasing accuracy of navigation during surgical procedures.

Turning first to FIG. 1A, a block diagram of a system 100 according to at least one embodiment of the present disclosure is shown. The system 100 may be used, for example: to carry out one or more aspects of the method disclosed herein; for navigation purposes; for registration purposes; for calibration operations; to verify (automatically or manually) operational integrity of a navigation system (such as the navigation system 160), of a robot (such as a robot 136), or of any other component or device having encoders or other sensors; or for any other useful purpose. The system 100 comprises a computing device 102, a tracking marker sensor 132, a robot 136, a navigation system 160, a database 164, and a cloud 168. Notwithstanding the foregoing, systems according to other embodiments of the present disclosure may omit any one or more of the computing device 102, the tracking marker sensor 132, the robot 136, the navigation system 160, the database 164, and/or the cloud 168. Additionally, systems according to other embodiments of the present disclosure may arrange one or more components of the system 100 differently (e.g., one or more of the tracking marker sensor 132, the robot 136, and the navigation system 160 may comprise the components shown in FIG. 1A as being part of the computing device 102).

The computing device 102 comprises at least one processor 104, at least one communication interface 108, at least one user interface 112, and at least one memory 116. A computing device according to other embodiments of the present disclosure may omit one or both of the communication interface(s) 108 and the user interface(s) 112.

The at least one processor 104 of the computing device 102 may be any processor identified or described herein or any similar processor. The at least one processor 104 may be configured to execute instructions stored in the at least one memory 116, which instructions may cause the at least one processor 104 to carry out one or more computing steps utilizing or based on data received, for example, from the tracking marker sensor 132, the robot 136, the navigation system 160, the database 164, and/or the cloud 168.

The computing device 102 may also comprise at least one communication interface 108. The at least one communication interface 108 may be used for receiving image data or other information from an external source (such as the tracking marker sensor 132, the robot 136, the navigation system 160, the database 164, the cloud 168, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the tracking marker sensor 132, the robot 136, the navigation system 160, the database 164, the cloud 168, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, headset and/or any other device for receiving information from a user and/or for providing information to a user of the computing device 102. The at least one user interface 112 may be used, for example, to receive a user selection or other user input in connection with any step of any method (e.g., the method 200) described herein; to receive a user selection or other user input regarding one or more configurable settings of the computing device 102 and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the method 200 described herein. The at least one memory 116 may store, for example, information about one or more predetermined coordinate systems 120 (e.g., information about a robotic coordinate system or space, information about a navigation coordinate system or space, information about a patient coordinate system or space); instructions 124 for execution by the at least one processor 104, for example to cause the at least one processor 104 to carry out one or more of the steps of the method 200; and/or one or more algorithms 128 for use by the processor in carrying out any calculations necessary to complete one or more of the steps of the method 200, or for any other calculations. Such predetermined coordinate system(s) 120, instructions 124, and/or algorithms 128 may, in some embodiments, be organized into one or more applications, modules, packages, layers, or engines, and may cause the at least one processor 104 to manipulate data stored in the at least one memory 116 and/or received from or via another component of the system 100.

The tracking marker sensor 132 is operable to detect an arrangement of a base set of tracking markers 158 and at least one additional set of tracking markers 156 (described below). The tracking marker sensor 132 may be, for example, an optical camera; an infrared camera; a 3D camera system; a stereoscopic vision system; another imaging device; or any other sensor that can detect the at least one additional set of tracking markers 156. The tracking marker sensor 132 may comprise a dedicated processor for executing instructions stored in a dedicated memory of the tracking marker sensor 132, or the tracking marker sensor 132 may simply be configured to transmit data collected therewith to the computing device 102 or to another component of the system 100. Although shown in FIG. 1A as being in communication only with the computing device 102, in some embodiments, the tracking marker sensor 132 may be in communication with any one or more of the computing device 102, the robot 136, the navigation system 160, the database 164, and/or the cloud 168. Also, in some embodiments, the computing device 102 may comprise the tracking marker sensor 132, while in other embodiments, the navigation system 160 may comprise the tracking marker sensor 132. In still other embodiments, the robot 136 may comprise the tracking marker sensor 132.

The tracking marker sensor 132 may be positioned directly above an operating table or portion thereof, or above and to one side of an operating table or portion thereof, or in another convenient position within an operating room or other room housing the robot 136. The tracking marker sensor 132 may be positioned at a location selected to provide the tracking marker sensor 132 with a clear, unobstructed, and/or partially unobstructed view of the robot 136, including the robotic arm 144 (and thus of the base set of tracking markers 158 and the at least one additional set of tracking markers 156 fixedly secured to the robotic arm 144) during operation thereof. In some embodiments, the tracking marker sensor 132 is fixed, while in other embodiments, the tracking marker sensor 132 may be precisely movable (whether manually or automatically) in one or more directions (e.g., whether by a second robotic arm such as the robotic arm 144, or otherwise).

The tracking marker sensor 132 may be configured to capture data regarding sensed tracking markers of the base set of tracking markers 158 and/or the at least one additional set of tracking markers 156 only at a given moment in time. For example, where the tracking marker sensor 132 is a camera, the tracking marker sensor 132 may be configured to capture still images comprising the base set of tracking markers 158 and the at least one additional set of tracking markers 156. The tracking marker sensor 132 may be configured to capture such data at periodic intervals, or when commanded by a user (e.g., via a user interface 112), or upon a signal (generated either autonomously or in response to user input) from the computing device 102, the robot 136, and/or the navigation system 160.

The tracking marker sensor 132 may additionally or alternatively be operable to capture data corresponding to one or more tracking markers of the base set of tracking markers 158 and/or the at least one additional set of tracking markers 156 continuously, in real-time. In such embodiments, the tracking marker sensor 132 may provide a stream of real-time sensor data to the computing device 102, which may continuously process the sensor data to detect one or more tracking markers of the base set of tracking markers 158 and/or the at least one additional set of tracking markers 156. In some embodiments, the tracking marker sensor 132 may comprise more than one tracking marker sensor 132.

Figure 1B:
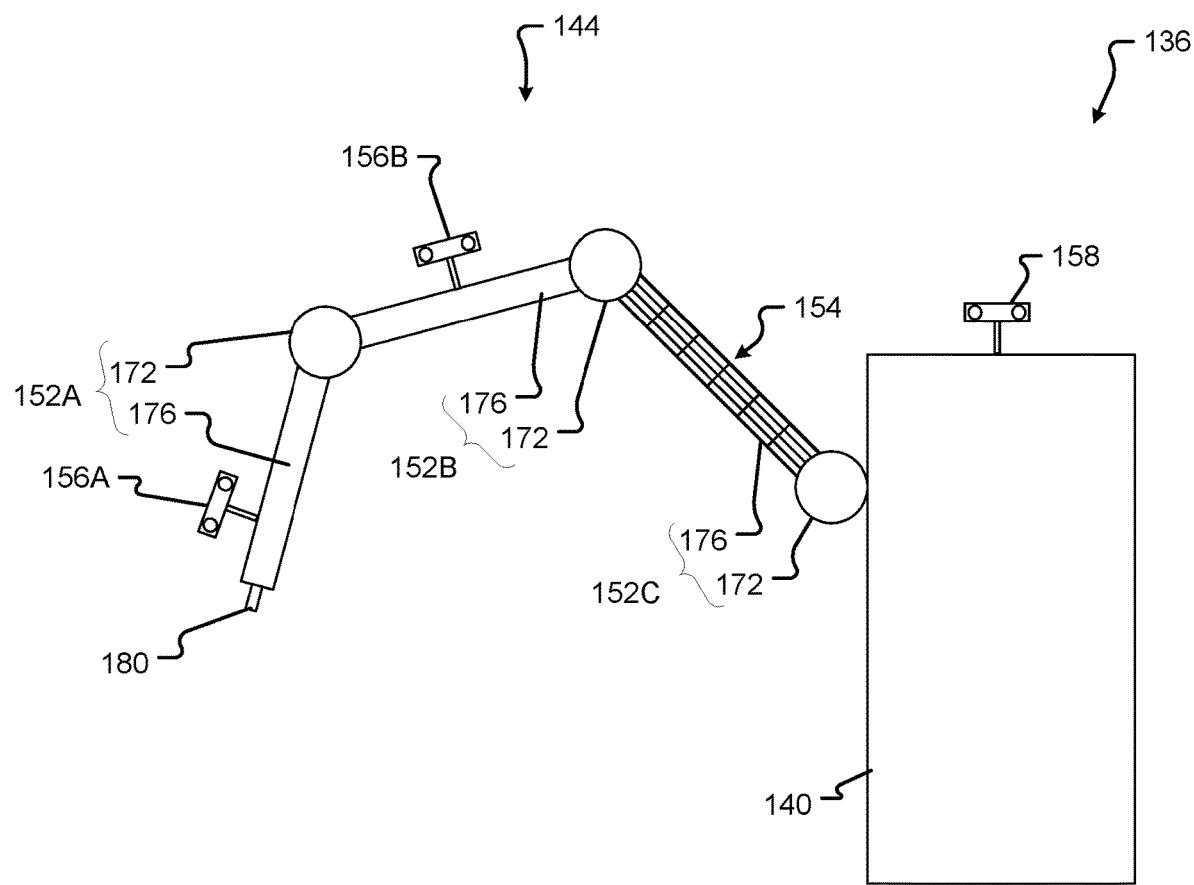
FIG. 1B depicts a robot according to at least one embodiment of the present disclosure.

With reference still to FIG. 1A, and also to FIG. 1B, the robot 136 may be any surgical robot or surgical robotic system. The robot 136 may be or comprise, for example, the Mazor X™ Stealth Edition robotic guidance system or the Mazor Robotics Renaissance™ Guidance System. The robot 136 may also be any device having a position sensor (e.g., an encoder) and/or distance sensor, including, for example, a microscope or a cranial biopsy tool. The robot 136 may comprise a base 140 that supports a robotic arm 144. The robot 136 may comprise one or more robotic arms 144. In some embodiments, the robotic arm 144 may comprise a first robotic arm and a second robotic arm. In other embodiments, the robot 136 may comprise more than two robotic arms 144. The robotic arm 144 may, in some embodiments, assist with a surgical procedure (e.g., by holding a tool in a desired trajectory or pose and/or supporting the weight of a tool while a surgeon or other user operates the tool, or otherwise) and/or automatically carry out a surgical procedure.

Referring still to FIGS. 1A-1B, the robotic arm 144 may have one, two, three, four, five, six, or more degrees of freedom. The robotic arm may have linear, rotary, and/or any other type of joints. The robotic arm 144 may comprise one or more segments 152. Each segment 152 may comprise a member 176 and a joint 172 to which the member 176 is attached and/or from which the member 176 extends. The joint 172 may be secured, for example, to the base 140 or to the member 176 of another segment 152. The joint 172 may be any type of joint that enables selective movement of the member 176 relative to the structure to which the joint 172 is attached. For example, the joint 172 may be a pivot joint, a hinge joint, a saddle joint, or a ball-and-socket joint. The joint 172 may allow movement of the member 176 in one dimension or in multiple dimensions, and/or along one axis or along multiple axes.

In embodiments of the robot 136 comprising a robotic arm 144 with only one segment 152, the joint 172 of the segment 152 may be secured to the base 140, and the member 176 of the segment 152 may comprise a proximal end secured to the joint 172 and a distal end supporting an end effector. The end effector may be, for example, a tool (e.g., a drill, saw, imaging device) or a tool guide (e.g., for guiding a biopsy needle, ablation probe, or other tool along a desired trajectory). In some embodiments, the end effector may be a measurement item for measuring a property of an object or anatomical element. In other embodiments, the end effector may be a navigated marker.

In embodiments of the robot 136 comprising a robotic arm 144 with a plurality of segments 152, such as that illustrated in FIG. 1B, a third segment 152C may comprise a joint 172 secured to the base 140, and the member 176 of the first segment 152C may comprise a proximal end secured to the joint 172 and a distal end supporting a joint 172 of a second segment 152B. The member 176 of the second segment 152B may comprise a proximal end secured to the joint 172 of the second segment 152B and a distal end supporting a joint 172 of a first segment 152A, and so on. The member 176 of the final segment 152 may comprise a distal end that supports an end effector 180, which may be the same as or similar to the end effector described above. In such embodiments, the joints 172 of the various segments 152 may or may not be of the same type, and the members 176 of the various segments 152 may or may not be identical.

All or some of the joints 172 of the segments 152 of the robotic arm 144 may be powered (so as to be selectively controllable without physical manipulation by a human). Any one or more of electric, pneumatic, hydraulic, and/or other means may be used to selectively control movement of a member 176 about the joint 172. For example, each segment 152 may comprise a servo for selectively moving the member 176 of that segment 152 relative to the joint 172 of that segment 152.

The robotic arm 144 also comprises one or more sensors 148. Each sensor 148 may be positioned to detect a position of a member 176 of a given segment 152 relative to the joint 172 of the segment 152. For example, where the joint 172 of a given segment 152 is or comprises a hinge joint, a sensor 148 may detect an angular position of the member 176 relative to an axis of the hinge joint. Where the joint 172 of a given segment 152 is or comprises a rotary joint (e.g., configured to allow rotation of the member 176 about an axis that extends through the member 176 and the joint 172), the sensor 148 may detect an angular position of the member 176 relative to the axis that extends through the member 176 and the joint 172. Each sensor 148 may be, for example, a rotary encoder, a linear encoder, or an incremental encoder.

Data from the sensors 148 may be provided to a processor of the robot 136, to the processor 104 of the computing device 102, and/or to the navigation system 160. The data may be used to calculate a position in space of the robotic arm 144 relative to a predetermined coordinate system 120. For example, the robot 136 may calculate a position in space of the robotic arm 144 relative to a coordinate system having an origin at the position where the joint 172 of the first segment 152 of the robotic arm 144 is secured to the base 140. The calculation may be based not just on data received from the sensor(s) 148, but also on data or information (such as, for example, physical dimensions) corresponding to each segment 152 and/or corresponding to an end effector secured to the final segment 152. By way of example only, a known location of the proximal end of the robotic arm 144 (e.g., where a joint 172 of the first segment 152 is secured to the base 140), known dimensions of each segment 152, and data from the sensor(s) 148 about an orientation of the member 176 of each segment 152 relative to the joint 172 of each segment 152 may be used to calculate the path of the robotic arm through space.

Referring still to FIGS. 1A-1B, a base set of tracking markers 158 are fixedly secured to or positioned on the base 140. The at least one additional set of tracking markers 156 comprises a first set of tracking markers 156A fixedly secured to or positioned on a first robotic arm segment 152A and a second set of tracking markers 156B fixedly secured to or positioned on a second robotic arm segment 152B. As used herein, "fixedly secured" does not mean "permanently secured," and indeed the tracking markers of the base set of tracking markers 158 and/or the at least one additional set of tracking markers 156 may be detachable from the base 140, the first robotic arm segment 152A, and/or the second robotic arm segment 152B.

In some embodiments, the at least one additional set of tracking markers 156 is only one set of tracking markers. In other embodiments, the at least one additional set of tracking markers 156 includes two or more sets of tracking markers. As illustrated, the first set of tracking markers 156A may be positioned near the end effector 180, though the first set of tracking markers 156A may be disposed anywhere on the robotic arm 144. Multiple sets of tracking markers 156 may be used to create a redundancy of tracking markers 156 such that a reference frame may be determined from some of the tracking markers 156. Thus, if some of the tracking markers 156 are visibly blocked, then the reference frame may still be determined from the remaining visible tracking markers 156 and the base set of tracking markers 158.

In some embodiments, the tracking markers of the base set of tracking markers 158 and/or the at least one additional set of tracking markers 156 may be light-emitting diodes (LEDs). In other embodiments, the tracking markers of the base set of tracking markers 158 and/or the at least one additional set of tracking markers 156 may be passive markers. The tracking markers of the base set of tracking markers 158 and/or the at least one additional set of tracking markers 156 may all be identical, or one or more of the tracking markers of the base set of tracking markers 158 and/or the at least one additional set of tracking markers 156 may be different than another one or more of the tracking markers of the base set of tracking markers 158 and/or the at least one additional set of tracking markers 156. In some embodiments, one or more of the tracking markers of the base set of tracking markers 158 and/or the at least one additional set of tracking markers 156 may be configured to emit light at a first wavelength, and another one or more of the tracking markers of the base set of tracking markers 158 and/or the at least one additional set of tracking markers 156 may be configured to emit light at a second wavelength different than the first wavelength. Also in some embodiments, one or more of the tracking markers of the base set of tracking markers 158 and/or the at least one additional set of tracking markers 156 may be configured to reflect light at a first wavelength, while another one or more of the tracking markers may be configured to reflect light at a second wavelength that is different than the first wavelength. The emitted and/or reflected wavelengths of light of the embodiments described above may be wavelengths within a particular spectrum (e.g., wavelengths corresponding to red light versus wavelengths corresponding to blue light in the visible spectrum, or different wavelengths in the infrared spectrum) as well as wavelengths from different spectrums (e.g., a wavelength in the visible spectrum versus a wavelength in the infrared spectrum).

In some embodiments, one or more of the tracking markers of the base set of tracking markers 158 and/or the at least one additional set of tracking markers 156 may be or comprise an LED that pulses at a first frequency, and another one or more of the tracking markers of the base set of tracking markers 158 and/or the at least one additional set of tracking markers 156 may be or comprise an LED that pulses at a second frequency different than the first frequency. In some embodiments, the tracking markers of the base set of tracking markers 158 and/or the at least one additional set of tracking markers 156 may be or comprise reflective spheres, geometric patterns (such as, for example, QR codes), or other items or features that may be readily distinguished by the tracking marker sensor 132. In other embodiments, the tracking markers of the base set of tracking markers 158 and/or the at least one additional set of tracking markers 156 may be distinguishable wavelength (e.g., visible light (i.e., color), infrared, ultraviolet, etc.). For example, a first set of tracking markers may be a first wavelength and a second set of tracking markers may be a second wavelength. The tracking markers may be configured to be detectable by a tracking marker sensor 132 even when covered by a drape or other covering that may be arranged on or over the robotic arm 144 to maintain a sterile operating room environment.

In some embodiments, the number of tracking markers of the base set of tracking markers 158 and/or the at least one additional set of tracking markers 156 fixedly secured to or positioned on the robotic arm 144 and/or the base 140, respectively, may be at least two. In other embodiments, the number of tracking markers of the base set of tracking markers 158 and/or the at least one additional set of tracking markers 156 fixedly secured to or positioned on the base 140 and/or the robotic arm 144, respectively, may be more than two. The number of tracking markers of the base set of tracking markers 158 and/or the at least one additional set of tracking markers 156 may be positioned in any pattern and may be positioned on any portion of the robotic arm 144 and/or the base 140, respectively. The base set of tracking markers 158 may be positioned so as to be consistently detectable by the tracking marker sensor 132.

The number of sets of tracking markers 156 selected may be based on a minimum number of tracking markers the at least one additional set of tracking markers 156 needed to determine a position in space of the robotic arm 144 based on the relative orientation of the detected tracking markers of the at least one additional set of tracking markers 156 to the fixed, base set of tracking markers 158, as described in more detail below. For example, if the minimum number of additional tracking markers needed to determine a position of the robotic arm 144 (not counting the base set of tracking markers 158) is 2, then the robotic arm 144 may have only a single set of tracking markers 156 (comprising two or more tracking markers). Alternatively, if the minimum number of tracking markers needed to determine a position of the robotic arm 144 is 4, then the total number of tracking markers on the robotic arm 144 may be 4 or more markers defining one or more sets of tracking markers 156. The greater the multiple, the greater the likelihood that the minimum number of tracking markers will be visible to or otherwise detectable by the tracking marker sensor 132 regardless of the orientation of the robotic arm 144.

Referring to FIG. 1A, a pattern 154 (e.g., structured light) may be projected onto the robotic arm 144. The pattern 154 may be projected by a camera or a projector onto the robotic arm 144. In other embodiments, the pattern may be painted onto the robotic arm 144. The pattern 154 may reflect light in any wavelength. In some embodiments, the pattern 154 is a grid. In other embodiments, the pattern 154 may be any pattern, geometrical pattern, or combination of patterns. The pattern 154 may be projected on a portion of the robotic arm 144 or on the entire robotic arm 144. The pattern 154 may enable mapping of the robotic arm 144 when utilized with the tracking markers of the at least one additional set of tracking markers 156, as will be described in further detail.

Referring again to FIG. 1A, the navigation system 160 may provide navigation for a surgeon and/or for the robot 136 during an operation. The navigation system 160 may be any now-known or future-developed navigation system, including, for example, the Medtronic StealthStation™ S8 surgical navigation system. The navigation system 160 may include a camera or other sensor(s) for detecting and/or tracking one or more reference markers, navigated trackers, or other objects within an operating room or other room where a surgical procedure takes place. In some embodiments, the navigation system 160 may comprise the tracking marker sensor 132. In various embodiments, the navigation system 160 may be used to track a position of the robotic arm 144 (or, more particularly, of tracking markers 156 attached to the robotic arm 144). The navigation system 160 may be used to track a position of one or more reference markers or arrays or other structures useful for detection by a camera or other sensor of the navigation system 160. The navigation system 160 may include a display for displaying one or more images from an external source (e.g., the computing device 102, tracking marker sensor 132, or other source) or a video stream from the camera or other sensor of the navigation system 160. In some embodiments, the system 100 may operate without the use of the navigation system 160.

The database 164 may store information that correlates each particular arrangement of the at least one additional set of tracking markers 156 to a corresponding position and orientation, or pose, of the robotic arm 144. The database 164 may also store information that correlates the base set of tracking markers 158 to a corresponding position and orientation, or pose, on the base 140. In such embodiments, information from the tracking marker sensor 132 about the position of each of a plurality of detected tracking markers of the at least one additional set of tracking markers 156 may be used to look up, in the database 164, a corresponding position of the robotic arm 144. The database 164 may additionally or alternatively store, for example, information about or corresponding to one or more characteristics of the tracking markers of the base set of tracking markers 158 and/or the at least one additional set of tracking markers 156; one or more surgical plans for use by the robot 136, the navigation system 160, and/or a user of the computing device 102 or of the system 100; one or more images useful in connection with a surgery to be completed by or with the assistance of one or more other components of the system 100; and/or any other useful information. The database 164 may be configured to provide any such information to the computing device 102 or to any other device of the system 100 or external to the system 100, whether directly or via the cloud 168. In some embodiments, the database 164 may be or comprise part of a hospital image storage system, such as a picture archiving and communication system (PACS), a health information system (HIS), and/or another system for collecting, storing, managing, and/or transmitting electronic medical records including image data.

The cloud 168 may be or represent the Internet or any other wide area network. The computing device 102 may be connected to the cloud 168 via the communication interface 108, using a wired connection, a wireless connection, or both. In some embodiments, the computing device 102 may communicate with the database 164 and/or an external device (e.g., a computing device) via the cloud 168.

Figure 2:
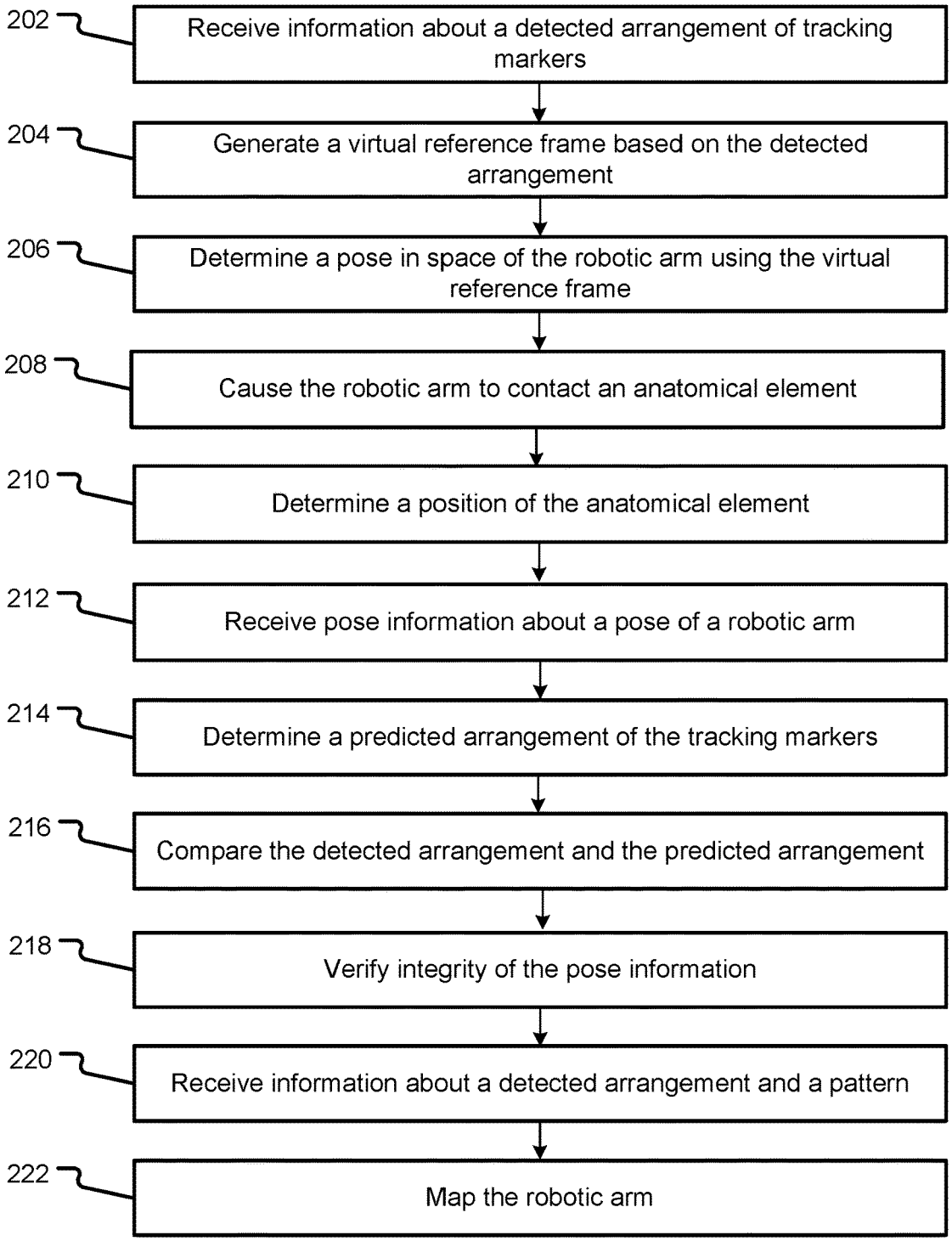
FIG. 2 is a flowchart of a method according to at least one embodiment of the present disclosure.

Turning now to FIG. 2, a method 200 for utilizing a robotic reference frame for navigation may be performed, for example, by at least one processor. The at least one processor may be the same as or similar to the processor(s) 104 of the computing device 102 described above. The at least one processor may be part of a robot (such as the robot 136) or part of a navigation system (such as the navigation system 160). A processor other than any processor described herein may also be used to execute the method 200. The at least one processor may perform the method 200 by executing instructions stored in a memory, such as the instructions 124 of the memory 116. The instructions may correspond to one or more steps of the method 200 described below. The instructions may cause the processor to execute one or more algorithms, such as the algorithms 128.

The method 200 comprises receiving information about a detected arrangement of a base set of tracking markers and at least one additional set of tracking markers (step 202). The base set of tracking markers may be the same as or similar to the base set of tracking markers 158 and the at least one additional set of tracking markers may be the same as or similar to the at least one additional set of tracking markers 156. The base set of tracking markers may be disposed on a base, such as the base 140, of a robot such as the robot 136. The at least one additional set of tracking markers may be disposed on a corresponding robotic arm segment such as the robotic arm segment 152 of a robotic arm such as the robotic arm 144. In some embodiments, the at least one additional set of tracking markers comprises a first set of tracking markers such as the first set of tracking markers 156A disposed on a first robotic arm segment such as the first robotic arm segment 152A and a second set of tracking markers such as the second set of tracking markers 156B disposed on a second robotic arm segment such as the second robotic arm segment 152B. In such embodiments, the detected arrangement may include information about the first set of tracking markers, the second set of tracking markers, or both sets of tracking markers.

The tracking markers may be the same as or similar to the tracking markers of the base set of tracking markers 158 and/or the at least one additional set of tracking markers 156 as described above. For example, the tracking markers may be LEDs, or reflective spheres, or geometric patterns such as QR codes. The tracking markers may all be identical, or each may be distinguishable from the others by a unique characteristic (e.g., a unique wavelength, a unique pulsating frequency). In some embodiments, some tracking markers may be distinguishable from one or more other tracking markers by a shared characteristic. For example, a first set of tracking markers may emit light at a first wavelength, and a second set of tracking markers may emit light at a second wavelength. In other embodiments, the tracking markers may be distinguishable by wavelength (whether due to variations in color or otherwise). For example, a first set of tracking markers may reflect light at a first wavelength and a second set of tracking markers may reflect light at a second wavelength.

The information may be received from a sensor. The sensor may be a tracking marker sensor, which may be the same as or similar to the tracking marker sensor 132. The tracking marker sensor may be an optical camera, an infrared camera, or any other sensor configured to detect the tracking markers. The tracking marker sensor, in some embodiments, may be part of the robot, or part of a navigation system such as the navigation system 160, or part of a computing device such as the computing device 102. In some embodiments, the tracking marker sensor may be independent of any of the foregoing components, but may be in electronic communication with one or more of the foregoing components.

The information may comprise a position of each of the base set of tracking markers and the at least one additional set of tracking markers in a detected arrangement of tracking markers. The position of the detected arrangement of tracking markers may be defined based on a coordinate system (such as a robotic coordinate system or a navigation coordinate system) or relative to another one or more of the base set of tracking markers and the at least one additional set of tracking markers. The information may comprise only information about a position of each of the base set of tracking markers and the at least one additional set of tracking markers relative to each other, and may be useful for calculating a position of each of the base set of tracking markers and the at least one additional set of tracking markers relative to a coordinate system (such as a robotic coordinate system or a navigation coordinate system).

The information may be received, for example, via a communication interface such as the communication interface 108.

The method 200 also comprises generating a virtual reference frame based on the detected arrangement (step 204). The virtual reference frame beneficially enables use of a large (and therefore more accurate) virtual reference frame comprising the base set of tracking markers as well as at least one additional set of tracking markers disposed on a robot arm. The at least one additional set of tracking markers can be smaller than a standard physical reference frame because it does not have to provide the full functionality of a reference frame by itself. As a result, it occupies a smaller volume or area on or proximate the robotic arm, and is less likely to get obstruct a needed trajectory or line of sight during a surgical procedure. Moreover, where multiple sets of tracking markers are affixed to or otherwise connected to the robotic arm, any given movement of the robotic arm may cause one or more of the sets of tracking markers to be obscured from view of a tracking marker sensor, while also causing one or more other sets of tracking markers to come into view of the tracking marker sensor. As a result, a virtual reference frame can still be constructed and utilized as the robotic arm is used.

The method 200 also comprises determining a pose in space of the robotic arm using the virtual reference frame (step 206). Because at least one robotic arm segment correlates to the at least one additional set of tracking markers (e.g., because the at least one additional set of tracking markers is secured to the at least one robotic arm segment), a pose of the at least one robotic arm segment is known based on the pose of the at least one additional set of tracking markers. Also, because a base of the robot correlates to the base set of tracking markers (e.g., because the base set of tracking markers is secured to the base of the robot), a pose of the base is known from the pose of the base set of tracking markers. Thus, the pose of the at least one additional set of tracking markers relative to the base set of tracking markers correlates to a pose of the at least one robotic arm segment relative to the base. As such, the virtual reference frame can be used to determine the pose in space of the robotic arm. Alternatively, in embodiments where any given arrangement of the various tracking markers that make up the virtual reference frame can correspond to only one pose of the robotic arm, the virtual reference frame as a whole can be used to determine a pose of the robotic arm. In still further embodiments, even where a given arrangement of the various tracking markers that make up the virtual reference frame can correspond to multiple poses of the robotic arm, the virtual reference frame as a whole can be used to confirm an expected pose of the robotic arm (e.g., based on one or more sensors on or operably connected to the robotic arm). This may be accomplished, for example, simply by confirming that the pose of the robotic arm based on information from the sensors is one of the multiple poses of the robotic arm that corresponds to the detected arrangement of the various tracking markers that make up the virtual reference frame, as will be further described below.

The method 200 comprises causing a robotic arm to contact an anatomical element (step 208). In some embodiments, the robotic arm may alternatively contact an object such as a tool, instrument, or any other component. The robotic arm may contact the anatomical element using an end effector such as the end effector 180. In some embodiments, the end effector may be a navigated marker, which may be used to determine or verify a position of the anatomical element. In some embodiments, the robotic arm may be oriented by a user to contact the anatomical element. In other embodiments, the robotic arm may be oriented automatically. Sensed data from a sensor such as the robotic sensor 148 (e.g., a pressure sensor), from another sensor such as the tracking marker sensor 132 (e.g., an optical camera), or a combination of sensors may be used guide the robotic arm to contact the anatomical element.

The method 200 also comprises determining a position of the anatomical element (step 210). Determining the position can include determining a pose of the anatomical element. When the robotic arm is in contact with the anatomical element as described in step 208, the position of the anatomical element can be determined from the pose of the robotic arm. The pose of the robotic arm may be determined as described in steps 202-206. In other words, for example, step 208 may occur to orient the robotic arm to contact an anatomical element, then steps 202-206 may occur to determine a pose of the robotic arm, then step 210 may occur to determine a position of the anatomical element based on the pose of the robotic arm.

The position of the anatomical element can be determined based on a pose of the robotic arm in contact with the anatomical element. The position at a point of contact between the robotic arm and the anatomical element may be set as the position of the anatomical element. Alternatively, the position of the anatomical element can be determined by adding an offset to the point of contact or by using a model of the anatomical element to define a volume with a position corresponding to that of the anatomical element. Where an offset is used the offset may be based on a dimension of the anatomical element. Further, the steps 208-210 (as well as the steps 202-206) may be used to obtain a plurality of positions of the anatomical element to determine a boundary or surface of the anatomical element.

The method 200 also comprises receiving pose information about a pose of the robotic arm (step 212). The information may be received from a sensor, such as the sensor 148, positioned on or integrated with the robotic arm. In some embodiments, the sensor for detecting the arrangement of tracking markers as described in step 202 is a first sensor and the sensor for providing pose information is a second sensor. For example, the first sensor may be a navigation camera for detecting the arrangement of tracking markers and the second sensor may be an encoder for sensing a pose of the robotic arm.

The pose information received from the second sensor may comprise sensor data about a detected position and/or orientation of one or more segments of the robotic arm and/or of the robotic arm as a whole. The pose information may be based on one or more settings of one or more components of the robotic arm. For example, the pose information may comprise data describing a position (whether an actual position or a commanded position) of one or more motors, servos, gears, or other devices or components used to control a position of the robotic arm and/or one or more segments thereof. The pose information may be obtained independently of the detected arrangement information, and vice versa.

The method 200 also comprises determining, based on the pose information of a robotic arm received from the second sensor, a predicted arrangement of the base set of tracking markers and the at least one additional set of tracking markers (step 214). In some embodiments, the pose of the robotic arm may be a current pose of the robotic arm. In such embodiments, the current pose of the robot arm may be received from step 212. The determining may comprise accessing stored information—whether from a memory such as the memory 116, a database such as the database 164, or elsewhere—about a position of the base set of tracking markers relative to the base and each set of the at least one additional set of tracking markers relative to a corresponding at least one robotic arm segment of the robotic arm or a portion thereof. The determining may further comprise calculating a predicted position of each of the base set of tracking markers and the at least one additional set of tracking markers based on the planned position of the robotic arm and information about a position of each of the at least one additional set of tracking markers relative to the robotic arm (or a portion thereof). The determining may comprise calculating a predicted position of every tracking marker fixedly secured to the robotic arm, or only of a subset of every tracking marker fixedly secured to the robotic arm. The determining may further comprise compiling the calculated predicted positions of each of the plurality of tracking markers into a predicted arrangement of the plurality of tracking markers.

The predicted arrangement of the robotic arm may be determined relative to a coordinate system. The coordinate system may be a robotic coordinate system, a navigation coordinate system, or another coordinate system.

The method 200 also comprises comparing the detected arrangement of the base set of tracking markers and the at least one additional set of tracking markers received from the first sensor to the predicted arrangement of the base set of tracking markers and the at least one additional set of tracking markers (step 216). The comparing may comprise translating or otherwise correlating the predicted position of each of the base set of tracking markers and the at least one additional set of tracking markers from one coordinate space (e.g., a robotic coordinate space) to another coordinate space (e.g., a navigation coordinate space). Alternatively, the comparing may comprise translating or otherwise correlating the detected position of each of the base set of tracking markers and the at least one additional set of tracking markers from one coordinate space (e.g., a navigation coordinate space) to another coordinate space (e.g., a robotic coordinate space). The comparing may comprise simply comparing the relative positions of the base set of tracking markers and the at least one additional set of tracking markers in the predicted arrangement to the relative positions of the base set of tracking markers and the at least one additional set of tracking markers in the detected arrangement.

The method 200 also comprises verifying an integrity of the pose information (step 218). In some embodiments, a predetermined threshold may be used to determine if the pose information is verified. In such embodiments, a calculated difference between the detected arrangement and the predicted arrangement may be compared to the threshold. The difference may be calculated based on a difference between positions, orientations, or both. If the difference is within the threshold, then the pose information may be verified.

When the comparison yields a conclusion that the detected arrangement matches the predicted arrangement, the precise pose of the robotic arm is known and validated. Thus, at that moment, the robotic arm (by virtue of the tracking markers fixedly secured thereto) constitutes a custom, one-time reference frame useful for the same purposes as any known reference frame—including, for example, to register a robotic coordinate system to a navigation coordinate system, and/or to determine or confirm a position of a given object in a particular coordinate system. The robotic arm may, for example, be positioned such that an end thereof is in contact with an anatomical feature, a surgical tool, or another object, such that the robotic arm comprises a reference frame based upon which the position of the anatomical feature, the surgical tool, or the other object may be determined or confirmed.

Also when the comparison yields a conclusion that the detected arrangement matches the predicted arrangement, the operational integrity of the robot and of the navigation system can be confirmed. This can be useful during surgical procedures as well as for initial calibration operations for the robotic system. On the other hand, when the comparison yields a conclusion that the detected arrangement does not match the predicted arrangement, even though the robotic arm is in the pose (e.g., the position and/or orientation) used to determine the predicted arrangement, a further conclusion can be reached that one or both of the robot and the navigation system lack operational integrity. Thus, when this occurs, a warning may be displayed to an operator of the robot and/or of the navigation system, and/or an audible sound may be played, via a user interface (such as, for example, the user interface 112 of the computing device 102, or a user interface specific to the robot or to the navigation system). Provision of such a warning to an operator of the robot and/or of the navigation system helps to ensure that the suspect operational integrity of the robot and/or of the navigation system can be investigated, and any errors corrected, before the robot and/or the navigation system are used further.

In some embodiments, where the detected arrangement of the base set of tracking markers and the at least one additional set of tracking markers is only slightly different than the predicted arrangement of the base set of tracking markers and the at least one additional set of tracking markers, another arrangement of the base set of tracking markers and the at least one additional set of tracking markers (e.g., based on a different pose of the robotic arm) may be predicted, and the camera or other tracking marker sensor may provide additional information about a second detected arrangement of the tracking markers (detected, for example, when the robotic arm is in the different pose). If the second detected arrangement of the base set of tracking markers and the at least one additional set of tracking markers is again only slightly different than the second predicted arrangement of the base set of tracking markers and the at least one additional set of tracking markers, then an error calculation and/or calibration process may be undertaken to determine an adjustment to be applied to any further predicted arrangement so that it matches the corresponding detected arrangement, or vice versa. In other words, if an offset between a predicted arrangement of the base set of tracking markers and the at least one additional set of tracking markers and a corresponding detected arrangement of the base set of tracking markers and the at least one additional set of tracking markers can be characterized by a constant or a derived equation, such that the offset can be incorporated into further comparisons of a predicted arrangement and a detected arrangement of the base set of tracking markers and the at least one additional set of tracking markers, then the operational integrity of the robot and/or of the navigation system may be confirmed.

The method 200 may also comprise receiving information about a pattern on the robotic arm in addition to the detected arrangement (step 220). The pattern may be the pattern 154 and may be projected onto the robotic arm. The pattern may be projected by a camera or a projector (e.g., as structured lighted) onto a portion of the robotic arm or on the entire robotic arm. In other embodiments, the pattern may be painted onto the robotic arm. The pattern may reflect light in any wavelength. In some embodiments, the pattern is a grid. In other embodiments, the pattern may be any pattern, geometrical pattern, or combination of patterns. The pattern may be detected by a sensor. The sensor may be a camera. In some embodiments, the sensor may be the same sensor as the tracking marker sensor. In other embodiments, the sensor detecting the pattern may be the same as the camera or projector projecting the pattern.

The method 200 may also comprise mapping a surface of the robotic arm based on the pattern and the detected arrangement (step 222). A pose, position, or location in space of the robotic arm may be determined from the mapping. In some embodiments, the mapping may include mapping a surface of the robotic arm. In other embodiments, the mapping may include mapping a position or location in space of an outer shell and/or a position of each joint of the robotic arm. The pattern may be received from step 214 and the detected arrangement may be received from step 202. The detected arrangement of the base set of tracking markers and the at least one additional set of tracking markers may be used to determine a pose of the robotic arm in space, as described in step 206. The pattern may then be used to map a surface of the robotic arm at the determined position. The mapped surface be used to generate a three-dimensional model of the robotic arm.

Distortions detected in the pattern may be used to determine a shape, contour, and/or relative position of the surface. For example, a grid may be projected onto the robotic arm and based on distortions detected in the grid (e.g., lines angling towards or away from each other, extended or shorted lines, etc.), contours and relative positions of the surface may be determined and mapped.

In some embodiments, an entirety of the robotic arm may be painted or otherwise colored with a single color that is readily distinguishable from other colors in an environment in which the robotic arm is used. Once a pose of the robotic arm is detected and/or confirmed (e.g., using a virtual reference frame as described above), the tracking marker sensor or another sensor (e.g., an optical camera or other imaging device) may be used to detect the entirety of the robotic arm, and to determine a pose of the entirety of the robotic arm. This may be useful, for example, when dimensions of the entirety of the robotic arm are not known.

The present disclosure encompasses embodiments of the method 200 that comprise more or fewer steps than those described above.

The systems and methods provided herein beneficially enable determining a pose of a robotic arm based on a base set of tracking markers and at least one additional set of tracking markers positioned on the robotic arm, confirm a pose of the robotic arm, or determine a pose of an anatomical element. Because the base set of tracking markers is fixed and a redundancy of tracking markers is created (whether by inclusion of multiple tracking markers in each set of the at least one additional set of tracking markers, or by inclusion of multiple sets of tracking markers on the robotic arm), visibility (or detection) of only some tracking markers of the at least one additional set of tracking markers (or only one set of the at least one additional set of tracking markers) is needed to determine the pose of the robotic arm. The systems and methods thus avoids line of sight issues and enables generation of a virtual reference frame to determine the pose of the robotic arm even if only some of the tracking markers are visible. Additionally, the virtual reference frame combined with pose information received from a robotic sensor enable validation of the determined pose of the robotic arm. The pose information and the virtual reference frame may also be used to determine a pose of an anatomical element when the robotic arm is in contact with the anatomical element. Thus, the virtual reference frame provides many useful benefits for determining a pose of a robotic arm and combined with pose information from the robotic arm, verifying the pose of the robotic arm or determining a pose of an anatomical element.

As may be appreciated based on the foregoing disclosure, the present disclosure encompasses methods with fewer than all of the steps identified in FIG. 2 (and the corresponding description of the method 200), as well as methods that include additional steps beyond those identified in FIG. 2 (and the corresponding description of the method 200).

Embodiments of the present disclosure may include one or more aspects described in U.S. Patent Application No. 63/036,130, entitled "Robotic Reference Frames for Navigation" and having a filing date of Jun. 8, 2020, the entirety of which is incorporated by reference herein.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A robotic navigation system, comprising:
   a robot base;
   a robotic arm comprising:
      a proximal end secured to the robot base;
      a distal end movable relative to the proximal end; and one or more arm segments between the proximal end and the distal end;
a base set of tracking markers secured to the robot base;
at least one additional set of tracking markers secured to at least one arm segment of the one or more arm segments;
a first sensor for detecting an arrangement of the base set of tracking markers and the at least one additional set of tracking markers;
a second sensor configured to provide pose information corresponding to the robotic arm;
at least one processor; and
a memory storing instructions for execution by the at least one processor that, when executed, cause the at least one processor to:
receive the pose information from the second sensor; and
determine, based on the pose information, a predicted arrangement of the base set of tracking markers and the at least one additional set of tracking markers.

2. The robotic navigation system of claim 1, wherein the at least one additional set of tracking markers comprises a first set of tracking markers secured to a first arm segment of the one or more arm segments and a second set of tracking markers secured to a second arm segment of the one or more arm segments.

3. The robotic navigation system of claim 2, wherein each of the base set of tracking markers, the first set of tracking markers, and the second set of tracking markers comprises at least two markers.

4. The robotic navigation system of claim 1, further comprising: a geometric pattern projected onto the robotic arm.

5. The robotic navigation system of claim 1, wherein the at least one additional set of tracking markers are distinguishable by wavelength.

6. The robotic navigation system of claim 1, wherein the base set of tracking markers is at least one of removably secured or fixedly secured to the robot base.

7. The robotic navigation system of claim 1, wherein the instructions, when executed by the at least one processor, further cause the at least one processor to:
receive information about a detected arrangement of the base set of tracking markers and the at least one additional set of tracking markers from the first sensor;
generate a virtual reference frame spanning the base set of tracking markers and the at least one additional set of tracking markers, based on the detected arrangement information; and
determine a pose in space of the robotic arm using the virtual reference frame.

8. The robotic navigation system of claim 4, wherein the instructions, when executed by the at least one processor, further cause the at least one processor to:
receive information about a detected arrangement of the base set of tracking markers and the at least one additional set of tracking markers and information about the geometric pattern projected onto the robotic arm; and
map, based on the detected arrangement and the geometric pattern, the robotic arm.

9. The robotic navigation system of claim 1, wherein the memory stores additional instructions for execution by the at least one processor that, when executed, further cause the at least one processor to: compare the detected arrangement to the predicted arrangement, the detected arrangement received from the first sensor.

10. The robotic navigation system of claim 9, wherein the memory stores additional instructions for execution by the at least one processor that, when executed, further cause the at least one processor to: verify the integrity of the pose information based on the comparison.

11. A method of utilizing a robotic reference frame for navigation, comprising:
causing a robotic arm to contact an anatomical element;
receiving information from a first sensor about a detected arrangement of a base set of tracking markers and at least one additional set of tracking markers, the base set of tracking markers positioned on a base of a robot and the at least one additional set of tracking markers positioned on a corresponding at least one robotic arm segment of the robotic arm;
generating a virtual reference frame based on the detected arrangement;
determining a position of the anatomical element based on the virtual reference frame;
receiving pose information from a second sensor;
determining, based on the pose information received from the second sensor, a predicted arrangement of the base set of tracking markers and the at least one additional set of tracking markers; and
comparing the detected arrangement to the predicted arrangement.

12. The method of claim 11, wherein the determining the position of the anatomical element includes determining a pose of the anatomical element based on the virtual reference frame.

13. The method of claim 11, wherein the at least one additional set of tracking markers comprises a first set of tracking markers secured to a first arm segment of the at least one arm segment and a second set of tracking markers secured to a second arm segment of the at least one arm segment.

14. The method of claim 11, wherein each of the base set of tracking markers and the at least one additional set of tracking markers comprises at least two markers.

15. The method of claim 11, wherein the at least one additional set of tracking markers is distinguishable by wavelength.

16. The method of claim 11, wherein the base set of tracking markers is at least one of removably secured or fixedly secured to the robot base.

17. A device for surgical navigation utilizing a robotic reference frame, comprising:
at least one processor; and
a memory storing instructions for execution by the at least one processor that, when executed, cause the at least one processor to:
cause a robotic arm to contact an anatomical element;
receive information from a first sensor about a detected arrangement of a base set of tracking markers and a first set of tracking markers, the base set of tracking markers disposed on a base of a robot and the first set of tracking markers disposed on an arm segment of a robotic arm;
generate a virtual reference frame based on the detected arrangement;
determine a pose in space of the anatomical element based on the virtual reference frame;
receive pose information from a second sensor;

determine, based on the pose information received from the second sensor, a predicted arrangement of the base set of tracking markers and the first set of tracking markers; and compare the detected arrangement to the predicted arrangement.

18. The device of claim 17, wherein the arm segment is a first arm segment of a plurality of arm segments of the robotic arm, and a second arm segment of the plurality of arm segments comprises a second set of tracking markers.

19. The device of claim 18, wherein each of the base set of tracking markers, the first set of tracking markers, and the second set of tracking markers comprises at least two markers.

20. The device of claim 18, further comprising a geometric pattern projected onto the robotic arm.

* * * * *